US006366085B1

(12) United States Patent
Yeshurun et al.

(10) Patent No.: US 6,366,085 B1
(45) Date of Patent: Apr. 2, 2002

(54) PROBE DEVICE FOR MEASURING A MAGNETIC FIELD VECTOR

(75) Inventors: Yosef Yeshurun, Ganei Tikvah; Yosef Abulafia, Kfar Saba; Yehoshua Wolfus, Kiryat Ono; Avner Shaulov, Jerusalem; Elia Zeldov, Rehovot; Daniel Majer, Givat-Shmuel; Hadas Shtrikman, Rehovot, all of (IL)

(73) Assignees: Bar-Ilan University, Ramat-Gan; Yeda Research and Development Company, Ltd., Rehovot, both of (IL)

( * ) Notice: Subject to any disclaimer, the term of this patent is extended or adjusted under 35 U.S.C. 154(b) by 0 days.

(21) Appl. No.: 08/927,203

(22) Filed: Sep. 11, 1997

(51) Int. Cl.[7] ............................................... G01R 33/12
(52) U.S. Cl. ........................ 324/263; 324/235; 324/238
(58) Field of Search ................................ 324/251, 240, 324/241, 242, 243, 235, 263, 238

(56) References Cited

U.S. PATENT DOCUMENTS 2,758,276 A * 6/1956 Foerster ....................... 324/254
3,617,874 A * 11/1971 Forster ......................... 324/263
3,710,236 A * 1/1973 Halsey et al. ................ 324/235

OTHER PUBLICATIONS

"Automatic Devices for the Measurement of Flux Density Gradients", H.W. Weber et al., Cryogenics, 1976 pp. 39 and 41.

"Local Magnetization Measurements in High Temperature Superconductors", D. Majer et al.; 1996 pp. 271–296.

"Three–axis Cryogenic Hall Sensor", J. Kvitkovic et al., Journal of Magnetism and Magnetic Materials, 1996, pp. 440–441.

* cited by examiner

Primary Examiner—Walter Snow

(57) ABSTRACT

A method and a measuring device for determining the spatial distribution of a magnetic field vector. At least a pair of sensor elements is provided. Each sensor element measures a component of the magnetic field vector. The sensor elements are aligned in a parallel, spaced-apart relationship along an axis parallel to the measured components.

41 Claims, 7 Drawing Sheets

PROBE DEVICE FOR MEASURING A MAGNETIC FIELD VECTOR

BACKGROUND OF THE INVENTION

1. Field of the Invention

The present invention relates to a measuring technique for measuring a magnetic field vector, particularly useful for mapping the distribution of electric currents in a sample in order to locate defects.

2. Description of the Background Art

Devices for measuring the distribution of a magnetic field are known and widely used. Such a device typically comprises either a single sensor, or probe, mounted for movement along the surface of a sample to be inspected, or a stationary arrangement comprising an array of such probes.

FIG. 1 illustrates the main principles of operation of the conventional magnetic sensor such as, for example, a Hall sensor. Hall sensors are based on the known Hall effect according to which a magnetic field applied to a semiconductor, along which an electric current flows, produces a voltage across the semiconductor in a direction perpendicular to the magnetic field and the current directions. A Hall sensor, generally designated 1, typically has an active element 2 and two pairs of ohmic contacts 2a–2b and 3a–3b. An electric current I flows between the contacts 2a–2b aligned in the direction x. This current I, the magnitude and direction of which are known from a calibration stage, in the presence of a perpendicular magnetic field, generates a respective Hall voltage $V_y$ in the contacts 3a and 3b aligned in a transverse direction y. As known, a Hall sensor is sensitive to that component of the magnetic field which is perpendicular to its surface. More specifically, the Hall voltage $V_y$ is responsive to the current flow I and to the strength of a magnetic field provided within the vicinity of the sensor 1 and directed perpendicular to the surface of the active element 2. Thus, a component $B_z$ of the magnetic field B is measured. All these particulars are well known per se and, therefore, need not be described in more detail.

It is appreciated that in order to determine the gradient of the magnetic field B, within the vicinity of a conductive material, and thereby the actual magnitude and direction of the electric currents inside the conductive material, the magnetic field at different locations relative to the conductor should be determined. Although this information may be obtained by moving a single Hall sensor across the conductor, stationary arrangements of linear Hall sensor arrays have been developed by producing a row of such sensors aligned in a straight line. FIG. 2 illustrates the geometrical arrangement of a device of this kind, generally designated 4, comprising a pair of Hall sensors 6 and 8. The device 4 is located within a magnetic field B which is either externally applied magnetic field or induced by an electric current. The sensors 6 and 8 are aligned in a line extending in a direction x. The magnetic field components $Bz_1$ and $Bz_2$ are measured independently by each of the sensors 6 and 8 by the way of direct measurement of $Vy_1$ and $Vy_2$. Hence, the gradient of the magnetic field component $B_z$ along the direction x can be calculated as:

$$\frac{\partial B_z}{\partial x} = \frac{B_{z_1} - B_{z_2}}{L} \quad (1)$$

wherein L is the known distance between the sensors 6 and 8.

A device of this kind is disclosed, for example, in the article "Automatic Devices for the Measurement of Flux Density Gradients", H. W. Weber et al., Cryogenics, 1976. The device comprises eleven field probes made of InSb and mounted on a narrow gap between the two halves of a sample. Output voltages of the probes are recorded simultaneously in order to provide a complete description of the magnetic field distribution at eleven positions along the sample radius.

Turning back to FIG. 2, it is understood that the smaller the dimensions of each of the sensor and the distance L between the sensors 6 and 8, the higher the resolution of the device 4. It is often the case that the local value of a magnetic field should be measured rather than global, for example for inspecting high temperature superconductors.

A device of this kind is disclosed, for example, in the article "Local Magnetization Measurements in High Temperature Superconductors", D. Majer et al. The device presents magnetization measurements in which a magnetic response to an externally applied field is investigated. The main purpose of the device is to provide local values of the magnetic induction B inside the sample. To this end, the device comprises arrays of substantially small Hall sensors each extending in a plane parallel to the sensors' surfaces and formed in a two dimensional electron gas (2DEG) material. These sensors have the advantage of a linear response to magnetic field, weak temperature dependence and high sensitivity. The advantage of 2DEG material is the ability to make several Hall sensors on the same device for measuring the magnetic induction across and outside the sample and giving a detailed local structure of the magnetic profile without limitation from sample's dimensions.

It is thus evident that according to the conventional approach as described above, the array of spaced parallel Hall sensors extends in the plane parallel to the sensors' surfaces. Each of the sensors measures the component $B_z$ of the magnetic field induction associated with respective location $(x_i;y_j)$ on the sample. If the array extends in the direction x, as exemplified in FIG. 2, the spatial distribution of the perpendicular component $B_z(x)$ is mapped.

However, the distribution of the other two components $B_x(x;y)$ and $B_y(x;y)$ of the magnetic field B, i.e. components parallel to the sensors' surfaces, cannot be measured by the conventional device employing magnetic sensors of any known kind. This information is very important, for example, for mapping electric currents inside a conductive material in order to make a useful diagnostic tool for finding features like cracks in the conductive material.

A device for measuring magnetic properties has been developed and disclosed in the article "Three-Axis Cryogenic Hall Sensor", J. Kvitkovic et al., Journal of Magnetism and Magnetic Materials, 1996. The device comprises three independent Hall sensors glued to a supporting ceramics and located at the corner edge thereof for detecting the spatial field profile within a small cube. The Hall sensors are arranged in such a manner that centers of their active areas are placed in three mutually perpendicular planes. The sensors are supplied by a single constant current source. A sample to be inspected is placed in an external magnetic field region. It is appreciated that such an arrangement of the device enables the magnetic field components to be measured along three directions x, y and z. However, the manufacturing and operation of the device are complicated requiring gluing processes and displacement of the device in order to obtain the map of a magnetic field vector.

It is often the case that a conductive structure has to be inspected without destroying the usefulness thereof. In other words, the contact to a conductive structure so as to directly connect it to a power source may be undesirable and/or impossible. Indeed, it turns out to be very difficult to place reliable electrical contacts on the surface of many conductive structures and in many cases a structure to be inspected in not accessible for attaching contacts. One of the conventional diagnostic techniques usually employed for inspecting such a conductive structure, the so-called 'eddy current technique', is based on the finding that an electric current flowing inside the structure is induced by an external alternating magnetic field. The standard way of measuring the magnetic field generated by eddy currents is based on the same process that generated the eddy currents, i.e. magnetic induction. A small coil, or array of small coils, is placed over the conductive structure and used for monitoring changes in the magnetic field patterns associated with the eddy currents.

However, the use of the magnetic induction method requires that the magnetic fields change in time. Additionally, such coils are sensitive to the rate of change, i.e. frequency, of the magnetic fields to be measured. When eddy currents are generated in a conductor by a changing magnetic field, the depth to which these currents are produced depends upon the frequency of the magnetic field. This is one of the reasons for the limited success of the conventional magnetic induction technique for structures made of good conductors such as, for example, aluminum used in aircraft structures, wherein eddy currents are produced only in a very thin layer near the surface of the structure. This penetration depth for alternating magnetic field greatly limits the applicability of the conventional eddy current method.

SUMMARY OF THE INVENTION

It is thus a major object of the present invention to provide a novel device for measuring a magnetic field distribution, particularly such a device for determining the complete 3D profile of a magnetic field vector.

It is a further object of the present invention to provide such a device that allows simultaneous measurements of the components of the magnetic field which are parallel and perpendicular to the surface of the device.

It is a still further object of the present invention to provide such a device that enables inspection of a conductive structure for detecting defects, if any, in a non-contact manner.

There is thus provided according to the most general aspect of the present invention a measuring device for determining the spatial distribution of a magnetic field vector, comprising at least a pair of sensor elements each for measuring a component of the magnetic field vector, the sensor elements being aligned in a parallel, spaced-apart relationship along an axis parallel to the measured components.

The term "component' as used herein should be understood to mean a projection of a vector on one axis of a cartesian coordinate system (i.e. along the "x", "y" or "z" axis).

The sensor elements are spaced from each other at a known small distance. The sensor elements are supported for a movement within a plane perpendicular to the axis of the alignment of the sensor elements. The magnetic field spatial distribution is determined by utilizing Maxwell's Laws for estimating the other two components of the magnetic field vector.

The device may comprise an array of a plurality of pairs of the sensor elements. The array may be a linear array or a two dimensional array. The array extends in a direction perpendicular to the axis of alignment of the sensor elements of each pair. The array may be supported for a movement within a plane perpendicular to the axis of the alignment of the sensor elements of each pair.

The magnetic field whose spatial distribution is to be determined is a field generated by an electric current passing through a conductive structure, wherein the device is accommodated within a vicinity of the conductive structure. The electric current may be a transport current generated by a power source directly coupled to the structure. In this case, the device may be used for quantitative determination of magnitude and direction of the transport current.

The electric current passing through the conductive structure may also be an 'eddy current' induced by an external, alternating, magnetic field applied to the conductive structure. In this case, the device may be used to evaluate a profile of the electric current inside the structure by comparing it to an associated reference data.

Each of the sensor elements may be a Hall sensor, coil, magneto-optic detector, etc. In case of Hall sensors, they may be formed in at least one pair of parallel, spaced-apart layers of semi-conductive materials, e.g. two-dimensional electron gases.

According to another aspect of the present invention, there is provided a method for determining the spatial distribution of a magnetic field vector within the vicinity of a conductive structure, comprising the steps of:
(a) bringing at least one pair of spaced parallel magnetic sensors each for measuring a component of a magnetic field vector in a vicinity of the conductive structure and aligning the sensors along a z axis parallel to the measured components;
(b) measuring with said at least one pair of magnetic sensors a gradient of the magnetic field component, $B_z(z)$; and
(c) determining at least one of the magnetic field components, $B_x(x;y)$ or $B_y(x;y)$ oriented perpendicular to one another in a plane perpendicular to said z axis.

The method may also comprise the step of calibration for determining the space between the sensors of said at least one pair of sensors. In the event that an external magnetic field is applied for inducing electric currents in the conductive structure, magnitude and direction of the external magnetic field may also be determined at the calibration step. The components $B_x(x;y)$ and $B_y(x;y)$ are determined by utilizing Maxwell's Laws.

The method may also comprise the step of estimating a profile of the electric current passing through the conductive structure either by utilizing Ampere's Law, or by comparing the determined distribution of the magnetic field vector within the vicinity of the conductive structure to a corresponding associated reference data.

According to yet another aspect of the present invention there is provided a method of fabricating a miniature measuring device for determining the spatial distribution of a magnetic field vector, comprising the steps of:
(i) providing a structure consisting of at least two parallel, spaced-apart layers each formed of a conductive material;
(ii) forming at least a first pattern of regions on one of said at least two layers so as to define at least one magnetic sensor;
(iii) forming at least a second pattern of regions on another of said at least two layers so as to define the at least one other magnetic sensor; and
(iv) fabricating said ohmic contacts within the formed patterns.

Step (i) preferably includes growth of the structure on an undoped semi-insulating substrate. The growth of the structure may be achieved by either chemical or physical deposition techniques such as, for example, molecular beam epitaxy or sputtering. The ohmic contacts may be formed by lithography and deposition processes as generally known.

More specifically, the present invention is used with Hall sensors and is therefore described below with respect to this application.

BRIEF DESCRIPTION OF THE DRAWINGS

In order to understand the invention and to see how the same may be carried out in practice, several preferred embodiments will now be described, by way of example only, with reference to the accompanying drawings, in which.

DETAILED DESCRIPTION OF THE PREFERRED EMBODIMENTS

Figure 1:
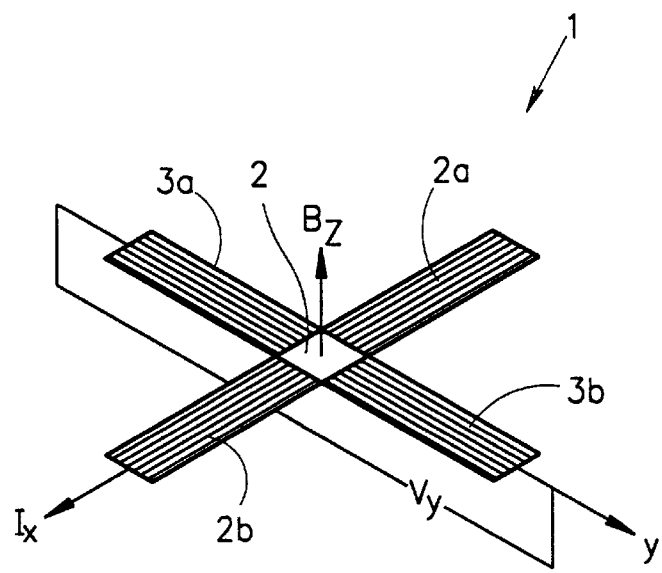
FIG. 1 is a schematic pictorial illustration of a conventional single Hall effect device.
Figure 2:
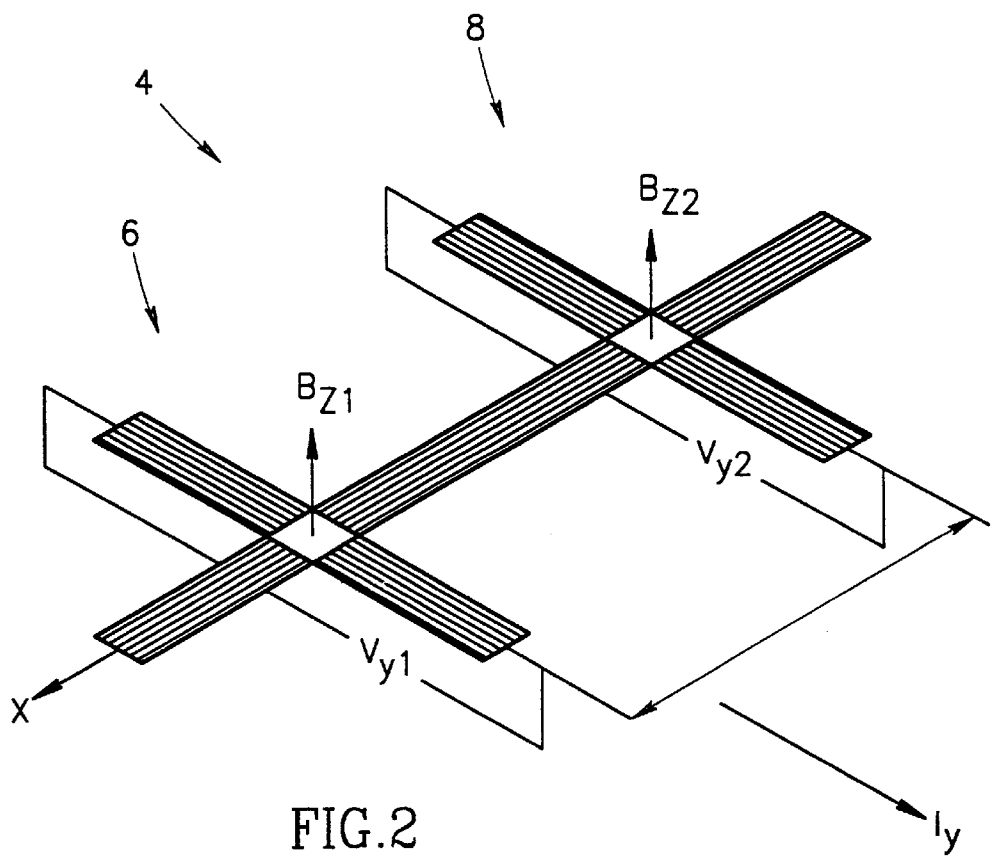
FIG. 2 is a schematic pictorial illustration of a conventional Hall sensor formed of a pair of the devices of FIG. 1.

FIG. 1 illustrates the main principles of operation of a conventional Hall sensor device. FIG. 2 illustrates the geometrical arrangement of a conventional magnetic gradiometer device.

Figure 3:
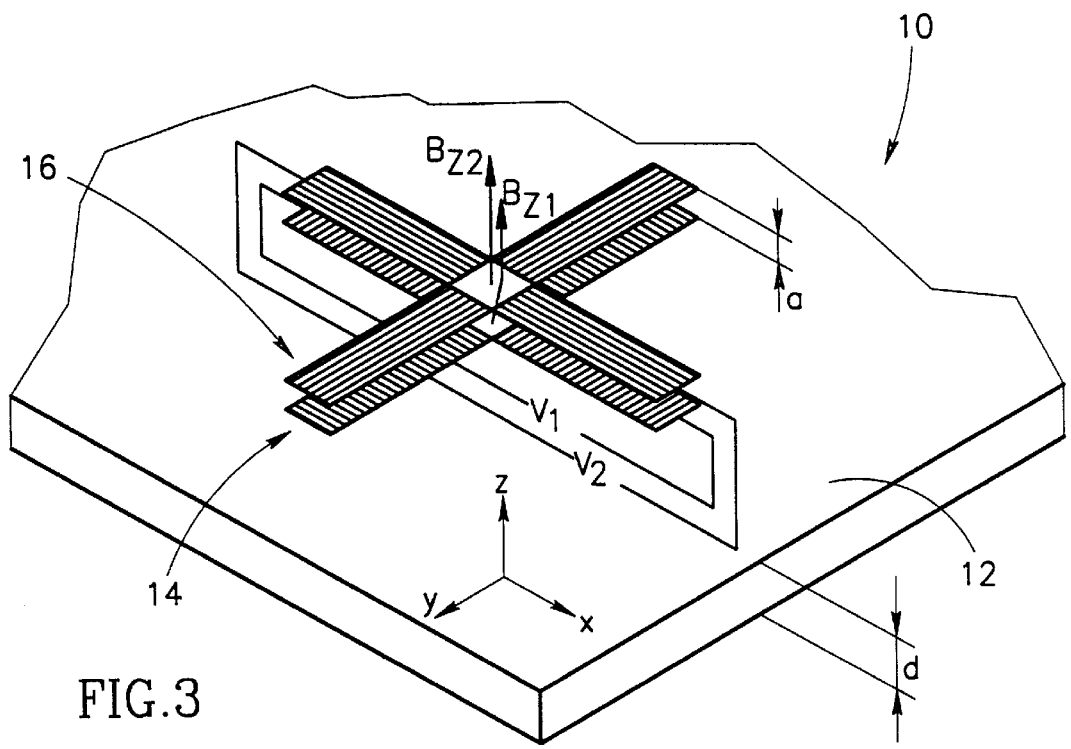
FIG. 3 is a schematic pictorial illustration of the main components of a measuring device according to a preferred embodiment of the present invention.

Referring to FIG. 3, there is shown a system, generally designated 10, for measuring the spatial distribution of a magnetic field within the vicinity of a specimen 12. The specimen 12 is coupled to a power source (not shown) for providing a current, I, inside the specimen 12 which flows in a direction y. It is appreciated that a magnetic field, B, is, therefore, provided in the vicinity of the specimen 12.

One of the essential features of the present invention is the provision of a pair of Hall sensors 14 and 16 arranged in a spaced parallel relationship along the direction z. Obviously, the Halls sensors 14 and 16 may be replaced by a pair of magnetic sensors of any other known kind such as, for example, copper coils. The sensors are spaced from each other by a small distance a. Such an arrangement may be achieved by any suitable means, for example, by gluing the sensors 14 and 16 either face-to-face or one on top of the other.

The sensor 14 measures the voltage $V_1$ at a first location $(x;y;z_1)$, while the sensor 16 measures the voltage $V_2$ at a second location $(x;y;z_2)$ relative to an origin. Hence, the sensors 14 and 16 present the corresponding values $Bz_1$ and $Bz_2$ of the magnetic field component perpendicular to their surfaces. The difference allows the determination of the gradient of the magnetic field component $B_z$ as follows:

$$\frac{\partial B_z}{\partial z} = \frac{Bz_1 - Bz_2}{a} \qquad (2)$$

These simple measurements enable the information about a second component of the magnetic field, $B_x$ or $B_y$, to be obtained in the case the third component being constant. Indeed, it is appreciated that the condition exists that one component $B_y$ is constant and the other two components are spatially dependent components $B_x=f(x)$ and $B_z=g(z)$. The magnetic field B must obey Maxwell's laws and can, therefore, be written as:

$$\nabla B = 0 \qquad (3)$$

$$-\frac{\partial B_z}{\partial z} = \frac{\partial B_x}{\partial x} + \frac{\partial B_y}{\partial y} \qquad (4)$$

$$-\int \frac{\partial B_z}{\partial z} dx = B_x + \int \frac{\partial B_y}{\partial y} dx + Const \qquad (5)$$

For $B_y$=Const, this gives:

$$-\int \frac{\partial B_z}{\partial z} dx = B_x + const \qquad (6)$$

Using the known Ampere's Law stating that the magnetic field B in the neighborhood of a conductor having a length l and carrying a current density I is related to the current density I by the equation:

$$\nabla B = \frac{4\mathcal{F}}{C} \cdot I \qquad (7)$$

Hence, for example for a platelet thin geometry of the specimen 12 the current value I can be calculated:

$$I = \frac{2Bx}{d} \qquad (8)$$

wherein d is a thickness of the specimen 22.

It is thus clear that the present invention enables the evaluation $B_x$ and, therefore, determination of the electric current I. It will be readily understood that the effect of scanning the conductor 12 by way of displacing the system 10 along the axes x and y provides the whole map of the magnetic field and, thereby, the current distribution inside the conductor 12. Alternatively, although not specifically shown, the system 10 may comprise more than two sensors aligned in the above described manner along the direction z. Additionally, the system 10 may be designed like a matrix comprising horizontal and vertical rows formed of Hall sensors.

It is appreciated that if the conductor 12 has an invisible defect such as, for example, a crack, the measurements of the gradient of the magnetic field component $B_z$ and determination of the actual magnitude and direction of the electric current I enables the existence of the crack to be detected and the location thereof inside the conductor 12 to be determined. Even in the case that precise calculations of the current profile cannot be easily done, a map of the magnetic field distribution provides enough information when compared to a respective reference data representative of a non-defect structure.

Figure 4:
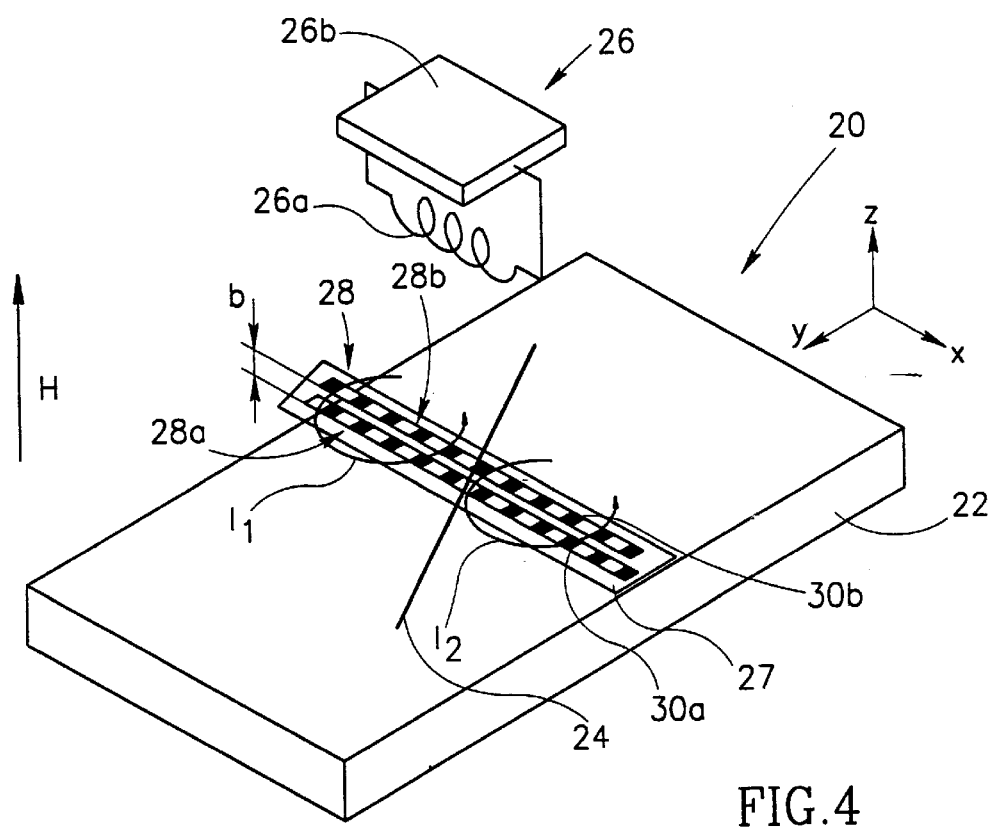
FIG. 4 is a schematic pictorial illustration of the main components of a measuring device according to an alternative embodiment of the present invention.
Figure 5A:
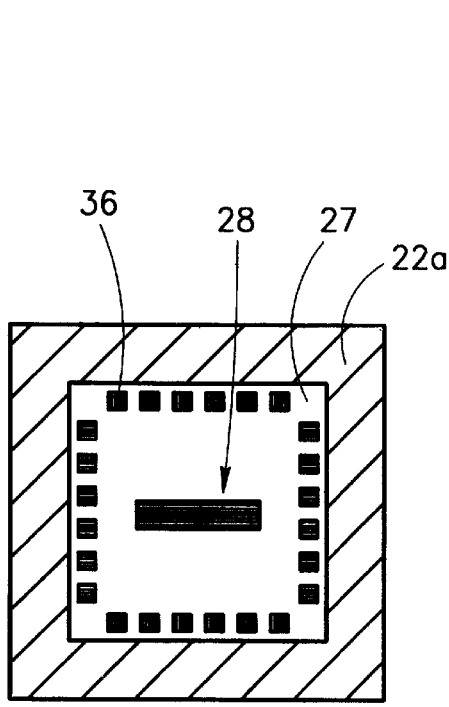
FIGS. 5a to 5b are schematic exploded top views more specifically illustrating sensors of the device of FIG. 4, but taken in an enlarged scale.
Figure 5B:
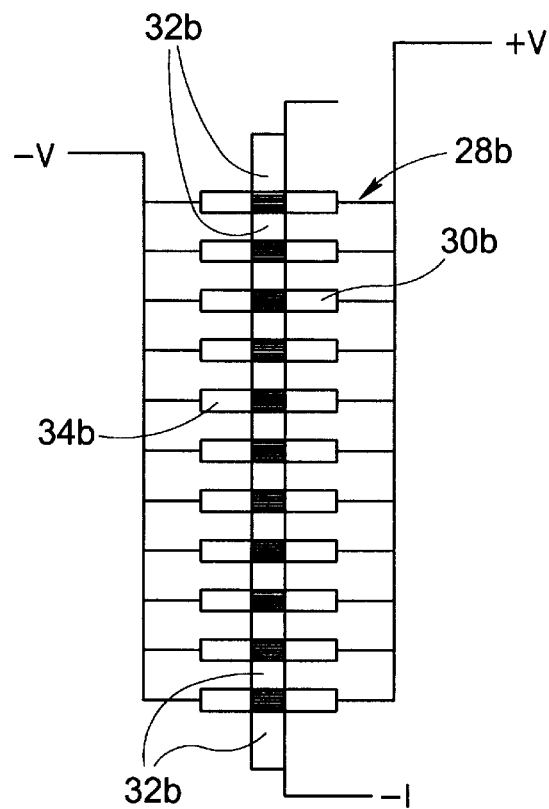

Turning now to FIG. 4, there is illustrated a system 20 constructed and operated according to another embodiment of the invention. The system 20 is associated with a specimen 22 formed of a conductive material having an invisible crack 24. The specimen 22 is a structural component of a bulk object (not shown) such as, for example, a printed circuit board. Therefore, the direct coupling of the specimen 22 to a power source for detecting the location of the crack 24 is unfeasible, the system 20 comprising instead an appropriate external generator, generally designated 26, for generating an alternating magnetic field for inducing eddy currents in the specimen 22. The generator 26 may be of any known kind. According to the present example of FIG. 4, the generator 26 includes a magnetic loop 26a connected to an alternating current source 26b. Obviously any other suitable means may be employed for the same purpose of providing an external, pulsed, magnetic field H in a region surrounding the specimen 22. Further provided is a measuring device 28 mounted proximate to the specimen 22 and coupled in a conventional manner to a control unit (not shown) so as to be operated thereby. The control unit does not form a part of the present invention and, therefore, need not be specifically described except to note that it provides imaging of the profile of an electric current passing through the specimen 22. The device 28 comprises an insulating substrate 27 on which lower and upper parallel rows 28a and 28b, respectively, are supported. The rows 28a and 28b are spaced from each other a small distance b. Each row is formed of eleven, electrically coupled Hall sensors each designated 30a and 30b, respectively, and having respective mutually perpendicular pairs of contacts. These contacts designated 32b and 34b for the sensors 30b are shown in FIG. 5b. The device 28 may be fabricated by any suitable technique. For example, the rows 28a and 28b may be glued to each other so as to be spaced apart by the glue layer having the thickness b. It is appreciated that the lower the distance b, the higher the resolution of the device 28.

Referring FIG. 5b, it will be clear that the sensors 30b of the row 28b are coupled to each other through those contacts 32b through which an electric current flows. Respective Hall voltage V is generated in contacts 34b. As shown in FIG. 5a, each sensor 32b is supported on the substrate 27 by connecting each one of its orthogonally oriented contacts 32b and 34b to a respective contact 36 formed on a periphery of the substrate 27. Obviously, although not specifically shown, the row 28a is arranged in the same manner. Additionally, although also not specifically shown, means are provided for slidingly moving the device 28 along the y direction so as to scan the specimen 22 in a conventional manner.

As is known, the applied alternating magnetic field induces 'eddy currents' in the electrically conductive structures located in the region of an alternating magnetic field. The flow pattern of eddy currents depends on various features of the conductive material. Eddy currents flow preferentially in the areas of higher thickness and lower resistance of the conductive material. Eddy currents I do not easily flow across the crack 24 and, instead, form closed loops $I_1$ and $I_2$ on either side of the crack 24 as shown in FIG. 4.

Figure 6:
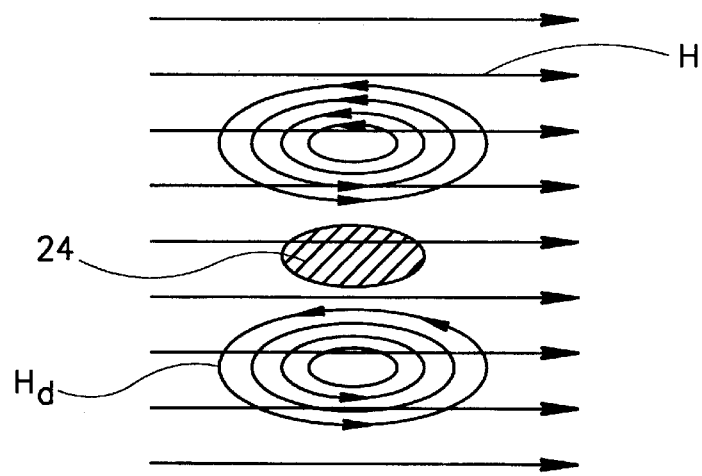
FIG. 6 schematically illustrates the main principles of operation of the device of FIG. 4.

Turning now to FIG. 6, there is illustrated the relationship between the flux from the applied field H and a flux from the magnetization $H_m$, i.e. generated by the eddy currents loops $I_1$ and $I_2$, which are induced by the magnetic field H. It will be readily understood that the measuring device 28 measures a magnetic field B which is defined as follows:

$$B = H - H_m,$$

wherein $H_m = N_d M$, $N_d$ being the known demagnetization factor, and M being a magnetic moment of currents contained in a unit volume of the specimen 22.

Hence, the measuring device 28, on the one hand, monitors by each of the Hall sensors in either row, 28a or 28b, position dependence of the magnetic field component $B_z(x)$ along the direction x. On the other hand, each pair of the sensors 30a–30b of both the row 28a and the row 28b concurrently monitors the gradient of the same component of the magnetic field $B_z(z)$ along the direction z. This enables the components $B_x$ and $B_y$ of the magnetic field vector B that are parallel to the surface of the specimen 22 to be estimated as described above. By measuring the surface-parallel components, a nearly direct measurement of the underlying electrical currents can be obtained. This is in contrast to using only the perpendicular field components which require measuring $B_z$ as a function of a position along the axis z and then performing integral-equation type calculations to determine the electrical currents as a function of position.

It should be specifically noted that, in distinction to the conventional induction method which produces data that contains complicated convolutions of properties, the present invention is based on the fact that the magnetic field is a fundamental physical property that is directly related to the flow of currents.

It is appreciated that by the way of changing a frequency of the external magnetic field H, different layers of the specimen 22 can be inspected. The higher the frequency, the higher the inspected layer within the specimen 22. Therefore, multilayered specimens such as, for example, multilayered circuit boards can be automatically inspected in a non-contact manner.

It is also appreciated that the measuring device 28 should be miniaturized in the case that either local measurements of the magnetic field B are required and/or the specimen 22 is of small dimensions. To this end, another essential feature of the present invention is the provision of such a miniature measuring device by the way of fabricating the rows 28a and 28b in a pair of spaced-apart, parallel layers each formed of a material suitable for use as a Hall sensor. Doped semiconductor layers or so-called 'semi-metals' may be employed such as, for example, two-dimensional electron gases (2DEGs).

Figure 7:
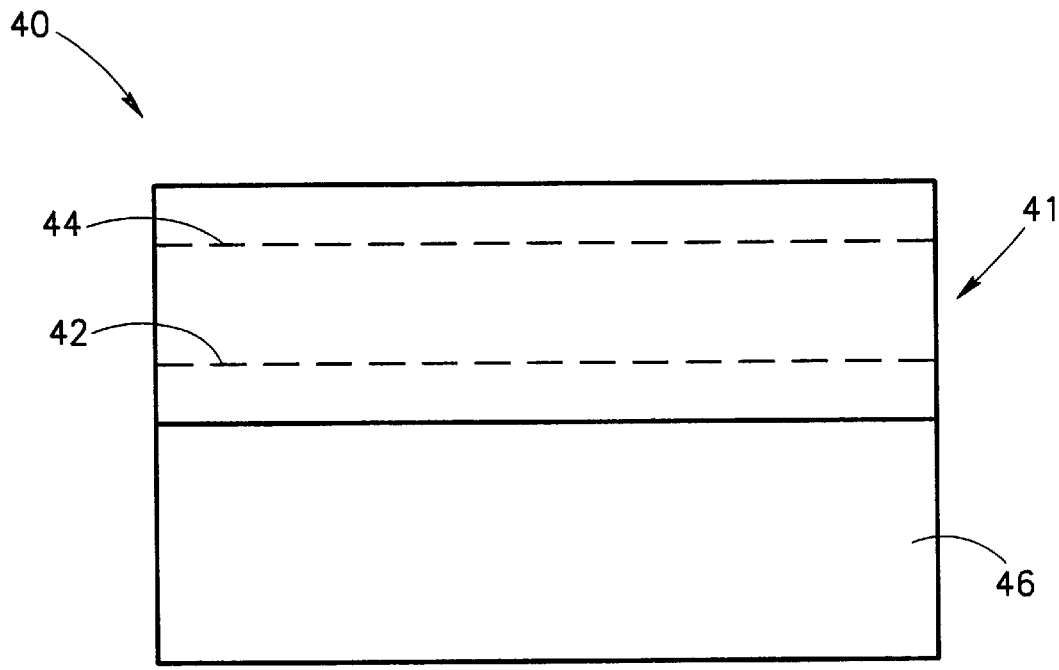
FIG. 7 schematically illustrates a wafer suitable for fabricating therefrom the sensor of FIG. 4.

Reference is now made to FIG. 7 illustrating a wafer, generally designated 40 which is used for fabricating the measuring device 28. The wafer 40 comprises a generic AlGaAs/GaAs heterostructure 41 formed of a lower 2DEG 42 and an upper 2DEG 44, which are grown on an undoped semi-insulating GaAs substrate 46. The structure 41 is grown in a molecular beam epitaxy system under the conventional growth conditions. Obviously, any other chemical or physical vapour deposition techniques may be employed such as, for example, sputtering. All these techniques are known per se and, therefore, need not be specifically described.

For example, although not specifically shown, the growth procedure comprises the following main steps. Initially, a buffer layer is grown which consists of 3000 Å undoped GaAs and a 20 period superlattice of AlGaAs/GaAs. The growth proceeds with a 6000 Å layer of undoped pure GaAs, a 300 Å 37% AlGaAs spacer, a 200 Å Si doped ($2.2 \cdot 10^{18}$ 1/cm$^3$) 37% AlGaAs layer. The carrier concentration in each 2DEG is determined by the thickness of the AlGaAs spacer which separates between the undoped high purity GaAs where the 2DEG resides, and the ionized (Si) impurities in the AlGaAs layer which supply the carriers to the underlying 2DEG. Thus, both 2DEGs are normal interface 2DEGs, namely the GaAs where the 2DEG resides is grown before the AlGaAs spacer and doping layer are grown. This is important for maintaining a mobility in both gases. The 2DEG is designed to have a carrier concentration of about $3 \cdot 10^{11}$ 1/cm$^2$ and a mobility of at least a few hundred thousand cm/V sec. The relatively high concentration of Al is chosen in order to ensure complete freeze-out of the excess Si and therefore prevent the presence of parallel conduction. The layer separating between two gases consists of the following sub-layers:

1) 1000 Å of AlGaAs ramped down from 37% to about 9% over 1000 Å;
2) 1000 Å of 9% AlGaAs;
3) a barrier of 2000 Å of 37% of AlGaAs; and
4) high purity 6000 Å thick GaAs layer.

Thus, the 2DEGs 42 an 44 are separated by about one micron of AlGaAs and GaAs. It is appreciated that the number of parallel 2DEGs can be further increased with a distance of about one micron between each two gases. Such structure allows to form a separate ohmic contact to each gas in a manner described below. The 37% AlGaAs prevents the penetration of the top ohmic contact to the lower lying gas. The low concentration AlGaAs prevents the formation of a parasitic 2DEG in between the two gases. The top 2DEG resides about 1000 Å below the surface of the structure 40. The spacer is 300 Å. The doping layer consists of a delta layer of Si with a concentration of about $1 \cdot 10^{12}$ 1/cm$^2$, and a uniformly doped 20 Å thick AlGaAs layer doped to $2.2 \cdot 10^{18}$ 1/cm$^3$. A thick layer of 100 Å of undoped AlGaAs separates between the doping layer and the 150 Å thick GaAs cap layer, which designed to reduce the leakage of a gate applied to the surface.

Figure 8A:
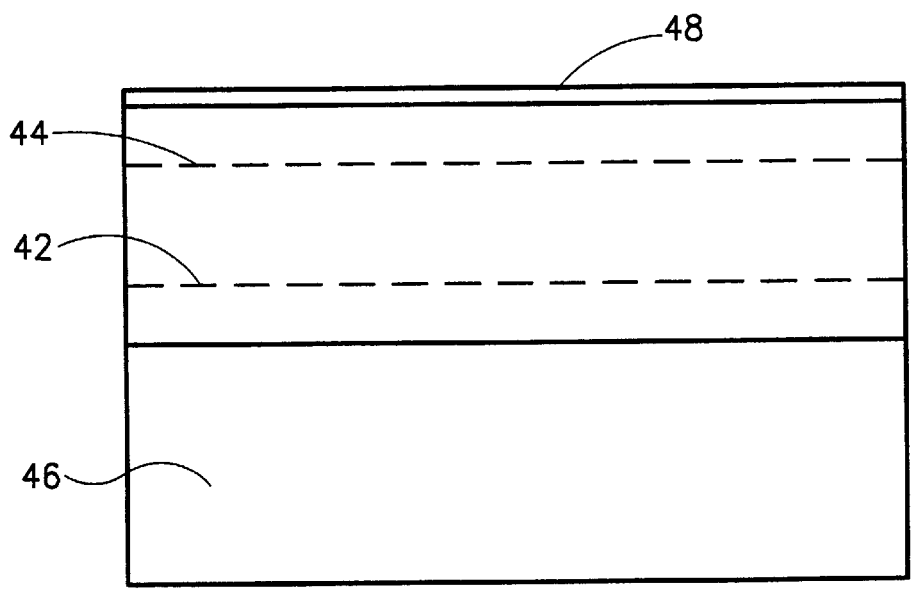
FIGS. 8a to 8g illustrate the main steps of a method according to the invention for fabricating a double-layer Hall sensor array using the wafer of FIG. 7.
Figure 8B:
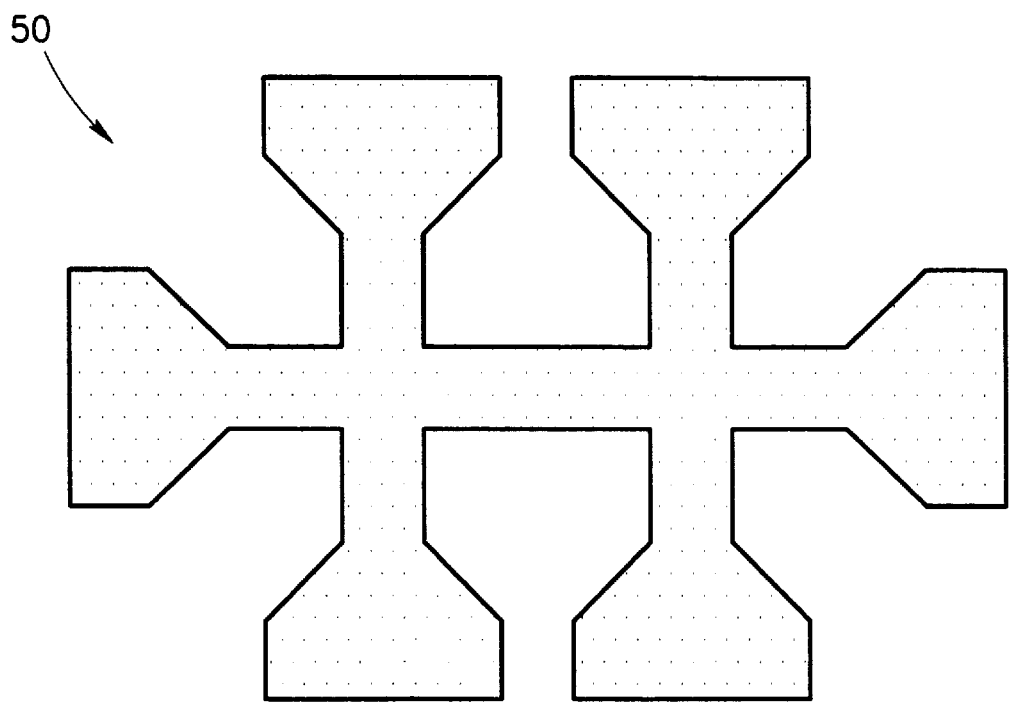
Figure 8C:
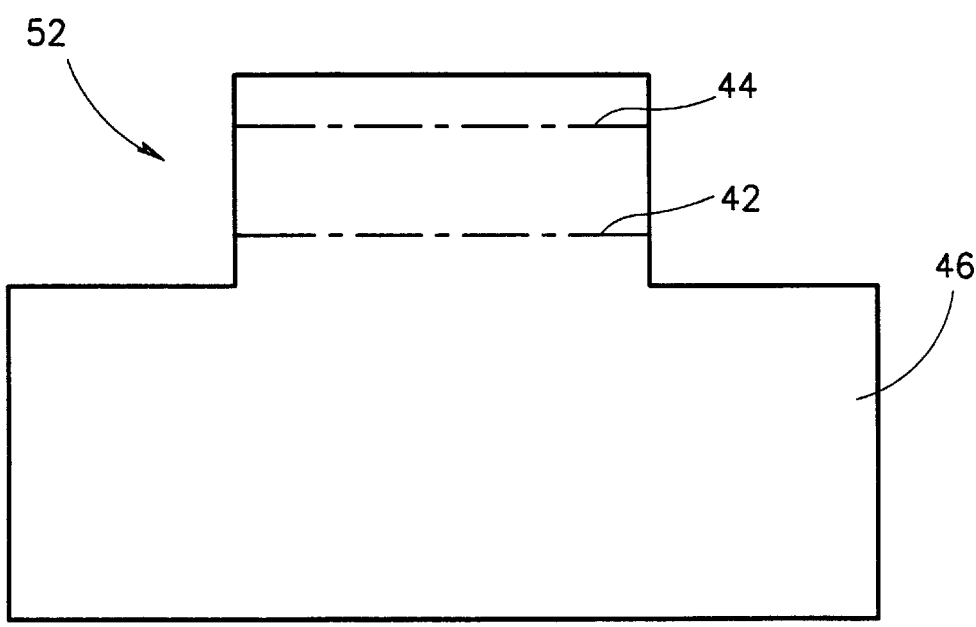
Figure 8D:
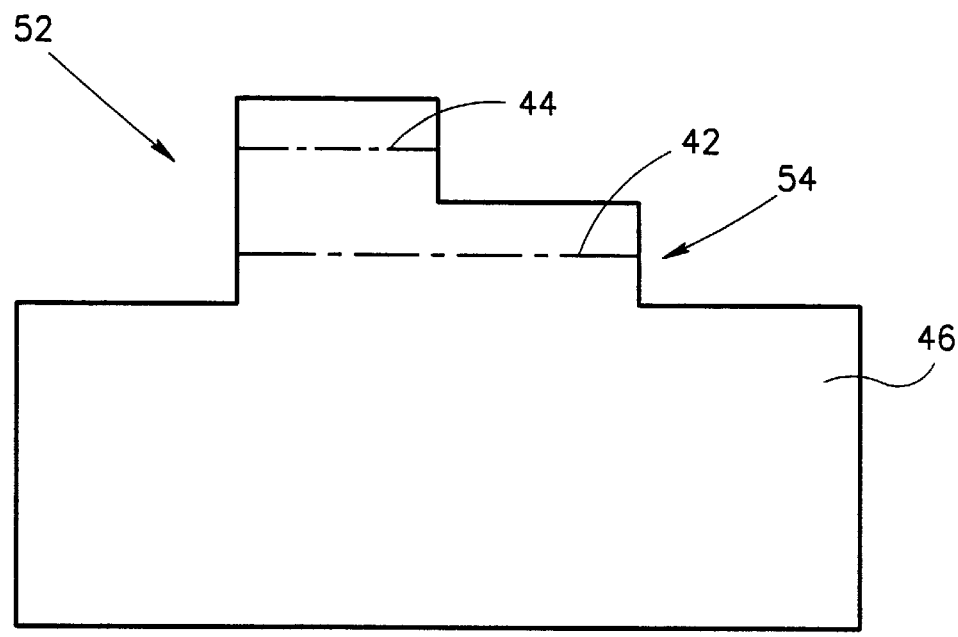
Figure 8E:
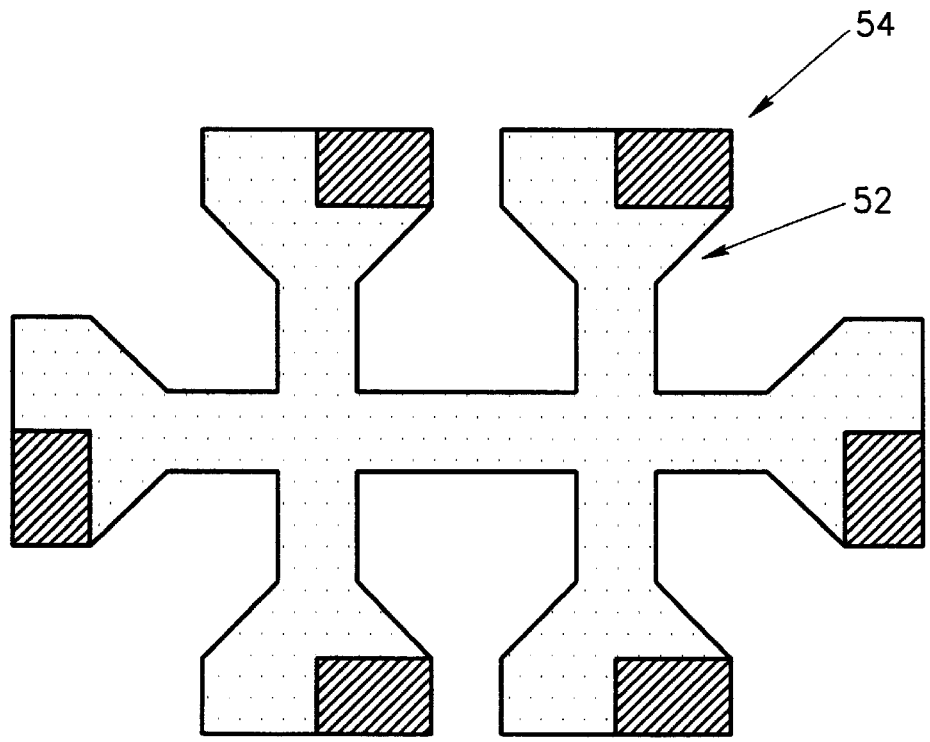
Figure 8F:
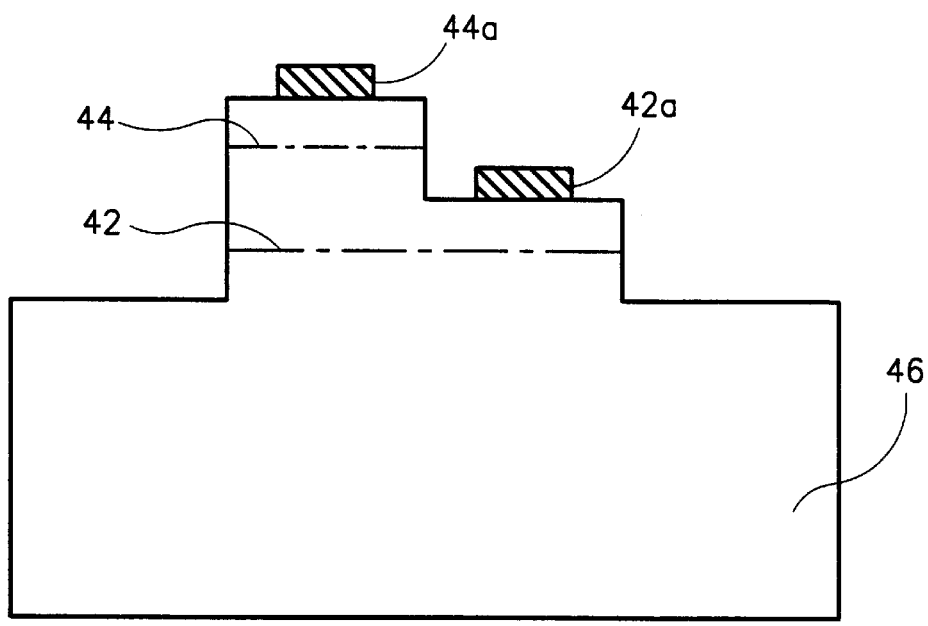
Figure 8G:
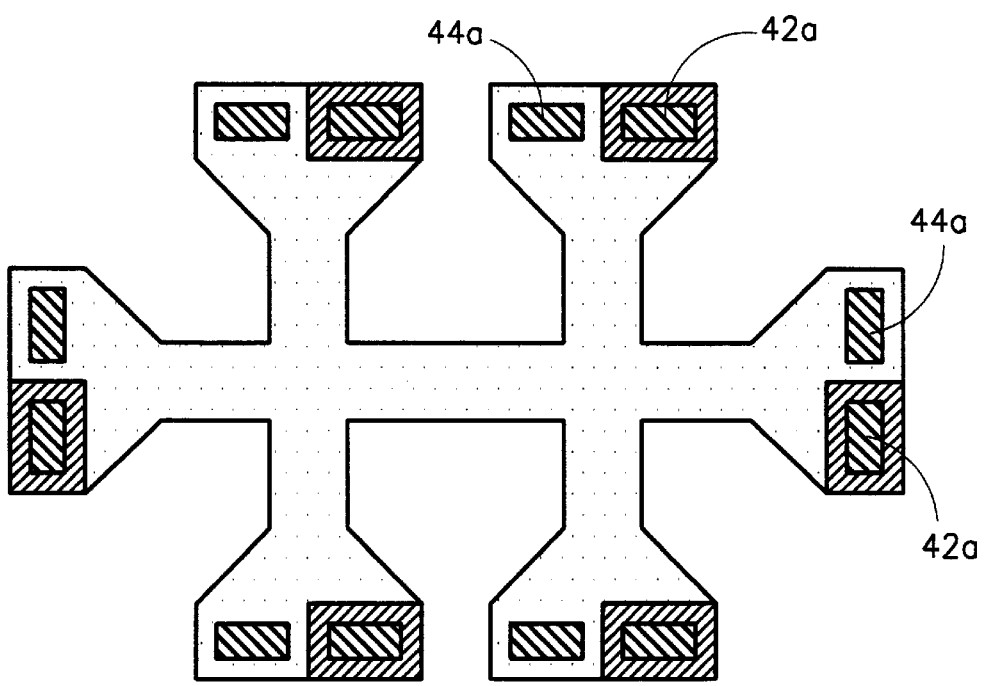

Turning now to FIGS. 8a–8g, the main steps of fabricating Hall sensors in the lower and upper 2DEGs 42 and 44 are illustrated. The wafer 40 is spin coated with a photoresist layer 48 (FIG. 8a) and the latter is exposed to light through a mask 50 (FIG. 8b). After development of the photoresist 48, the exposed layers (not shown) are chemically etched for obtaining a first mesa 52, the side view of which is shown in FIG. 8c. Both 2DEGs 42 and 44 are etched at all the areas outside the first mesa 52. Thereafter, although not specifically shown, the remaining photoresist is removed and a new spin coating with a photoresist layer is made. The exposure and chemical etching processes are, then, repeated using another mask so as to define a second mesa 54, which side and top views are illustrated in FIGS. 8d and 8e, respectively. Then, using lift off and evaporation processes in a conventional manner, the entire wafer is coated by several consecutive layers of metals Ni/GeAu/Ni/Au and alloyed at 450° C. resulting in ohmic contacts 42a for the lower layer 42. Further lift off, evaporation of metal layers and alloying processes result in ohmic contacts 44a for the upper layer 44 (FIGS. 8f and 8g). To this end, the metals which are deposited for making contacts 44a are Ni/GeAu/Nb/Au and the alloying temperature is about 390° C. It should be specifically noted that the provision of Nb layer, instead of conventionally used Ni layer, and relatively low alloying temperature prevents the upper contacts 44a from reaching the lower gas 42 and, thereby, avoids possible shorts. Finally, the obtained structure is etched either chemically or by reactive ion etching. It will be readily understood that six contacts 42a define a pair of lower Hall sensors, while six contacts 44a define a pair of upper Hall sensors. Each Hall sensor may thus be of less than $10\mu^2$ in size.

Those skilled in the art will readily appreciate that many modifications and changes may be applied to the invention as hereinbefore exemplified without departing from its scope defined in and by the appended claims. For example, the row having eleven Hall sensors is given by way of example only and any other number of sensors within the row, as well as more than one spaced parallel rows, may be employed. Additionally, the type of a magnetic sensor, the material used and the method of preparation of a magnetic sensor may be replaced by any other suitable means.

What is claimed is:

1. A measuring device for determining a spatial distribution of a magnetic field vector in a vicinity of a conductive sample, wherein the magnetic field is produced by an electric current passing through the conductive sample, the device comprising:

a probe including at least a pair of magnetic sensor elements aligned in a parallel spaced-apart relationship along a z-axis, each sensor element, when located in the vicinity of the sample, being operable for measuring a component $B_z$ of the magnetic field vector along said z-axis axis, the difference between the at least two measurements of said sensor elements along said z-axis being indicative of a gradient of the magnetic field component $B_z$ along said z-axis;

said pair of sensor elements being mounted for measuring the gradient of the magnetic field along said z-axis in at least two locations spaced apart along an x-axis perpendicular to said z-axis, the at least two measurements along the x-axis of the gradient of the magnetic field component alone said z-axis enabling the determination of said spatial distribution of the magnetic field vector which is indicative of a distribution of the electric current inside the conductive sample.

2. The device according to claim 1, wherein said sensor elements are spaced from each other at a known distance.

3. The device according to claim 1, wherein said sensor elements are supported for movement within a plane perpendicular to said axis of alignment of said sensor elements.

4. The device according to claim 1, wherein the spatial distribution of the magnetic field vector is determined by utilizing Maxwell's Laws for estimating two components of the magnetic field vector which are oriented perpendicular to one another in a plane perpendicular to said axis of alignment.

5. The device according to claim 1, comprising an array of a plurality of pairs of the sensor elements which extends in a direction perpendicular to the axis of alignment of the sensor elements of each pair.

6. The device according to claim 5, comprising a matrix formed of a plurality of said arrays aligned in a spaced-apart parallel relationship in a plane perpendicular to said axis of alignment of the sensor elements of each pair.

7. The device according to claim 5, wherein said array is supported for movement within a plane perpendicular to said axis of alignment of the sensor elements of each pair.

8. The device according to claim 1, wherein the electric current is a transport current generated by a power source directly coupled to the conductive sample.

9. A measuring device for determining a spatial distribution of a magnetic field vector in a vicinity of a conductive sample, wherein the magnetic field is produced by an electric current passing through the conductive sample, the electric current being an eddy current induced by an external, alternating, magnetic field applied to the conductive sample, the device comprising:

a probe, located in the vicinity of the conductive sample, comprising at least a pair of magnetic sensor elements aligned in a parallel spaced-apart relationship, each sensor element for measuring a component of the magnetic field vector along an axis of alignment of said sensor elements, said sensor elements being mounted for measuring a gradient of the magnetic field along said axis of alignment at at least two locations spaced apart along an axis perpendicular to said axis of alignment, thereby determining said spatial distribution of the magnetic field vector indicative of a distribution of the electric current inside the conductive sample.

10. The device according to claim 1, wherein each of said sensor elements is a Hall sensor.

11. The device according to claim 10, wherein said Hall sensors are formed in at least one pair of parallel, spaced-apart layers formed of semi-conductive materials.

12. The device according to claim 11, wherein said semi-conductive materials are two-dimensional electron gases.

13. The device according to claim 4, wherein said at least one pair of layers is formed of a pair of semi-metals.

14. A method for inspecting a conductive sample for defects by determining a spatial distribution of a magnetic field vector within a vicinity of the conductive sample, wherein the magnetic field is produced by an electric current passing through the conductive sample, the method comprising the steps of:

(a) bringing at least one pair of magnetic sensor elements aligned in a parallel spaced-apart relationship along a z axis in the vicinity of the conductive sample, each of the magnetic sensor elements for measuring a component of a magnetic field vector along the z axis;

(b) measuring with the magnetic sensor elements a gradient of a component $B_z(z)$ of the magnetic field vector along the z axis, at at least two locations spaced apart along an x axis perpendicular to the z axis; and (c) determining at least one of components $B_x(x;y)$ or $B_y(x;y)$ of the magnetic field vector, which are oriented perpendicular to one another in a plane perpendicular to the z axis, so as to provide a map of magnetic filed distribution indicative of distribution of the electric current inside the conductive sample.

15. The method according to claim 11, also comprising a step of calibration so as to determine parameters of the magnetic sensor elements.

16. The method according to claim 15, wherein said calibration step includes determination of a space provided between the magnetic sensor elements.

17. The method according to claim 11, wherein the electric current is passed through the conductive sample by coupling a power source to the conductive sample, the electric current being a transport current.

18. The method according to claim 11, wherein the electric current is passed through the conductive sample by applying an external alternating magnetic field to the conductive sample, the electric current being an eddy current induced by said external alternating magnetic field.

19. The method according to claim 11, wherein the step of determining at least one of components $B_x(x;y)$ or $B_y(x;y)$ of the magnetic field vector includes utilizing Maxwell's Laws.

20. The method according to claim 11, also comprising a step of determining a profile of the electric current passing through the conductive sample in order to detect defects in the conductive sample.

21. The method according to claim 20, wherein the profile of the electric current is determined by utilizing Ampere's Law.

22. The method according to claim 20, wherein the profile of the electric current is determined by comparing the determined spatial distribution of the magnetic field vector within the vicinity of the conductive sample to a reference data representative of a non-defect conductive sample.

23. The method according to claim 11, wherein each of the magnetic sensor elements is a Hall sensor.

24. The device of claim 1, wherein said probe is fabricated by a method comprising the steps of:

(i) providing a structure consisting of at least two parallel, spaced-apart layers each formed of a doped semiconductor material;

(ii) forming a first pattern of regions on one of said at least two layers so as to define one magnetic sensor element of said at least one pair of sensor elements;

(iii) forming a second pattern of regions on another of said at least two layers so as to define the other magnetic sensor element of said at least one pair of sensor elements; and (iv) fabricating contacts within the formed first and second patterns.

25. The device according to claim 24, wherein the step (i) includes growth of the structure on an undoped semi-insulating substrate.

26. The device according to claim 25, wherein the growth of the structure is achieved by deposition techniques.

27. The device according to claim 26, wherein said deposition technique comprises chemical vapor processes.

28. The device according to claim 26, wherein said deposition technique comprises physical vapor processes.

29. The device according to claim 28, wherein said physical vapor processes include molecular beam epitaxy.

30. The device according to claim 28, wherein said physical vapor processes include sputtering.

31. The device according to claim 24, wherein the contacts are formed by lithography and deposition processes.

32. The device according to claim 24, wherein each of the at least two magnetic sensor elements is a Hall sensor.

33. The method according to claim 11, wherein the step of measuring the gradient of the component $B_z(z)$ of the magnetic field vector at the at least two locations spaced apart along the x axis comprises the step of:

displacing the magnetic sensor elements along the x axis.

34. The method according to claim 11, wherein the step of measuring the gradient of the component $B_z(z)$ of the magnetic field vector at the at least two locations spaced apart along the x axis comprises the step of:

providing at least one additional pair of magnetic sensor elements, the at least two pairs being aligned in a parallel spaced apart relationship along the x axis.

35. A measuring device for determining a spatial distribution of a magnetic field vector in a vicinity of a conductive sample, wherein the magnetic field is produced by an electric current passing through the conductive sample, the device comprising:

a probe which includes at least a pair of magnetic sensor elements aligned in a parallel spaced-apart relationship, each sensor element for measuring a component of the magnetic field vector along an axis of alignment of said sensor elements;

said at least one pair of sensor elements being mounted for measuring a gradient of the magnetic field along said axis of alignment at at least two locations spaced apart along an axis perpendicular to said axis of alignment, thereby determining said spatial distribution of the magnetic field vector indicative of a distribution of the electric current inside the conductive sample;

said probe being fabricated by:

(i) providing a structure consisting of at least two parallel, spaced-apart layers formed of two-dimensional electron gases grown on an undoped semi-insulating substrate;

(ii) forming a first pattern of regions on one of said at least two layers so as to define one magnetic sensor element of said at least one pair of sensor elements;

(iii) forming a second pattern of regions on another of said at least two layers so as to define the other magnetic sensor element of said at least one pair of sensor elements; and (iv) fabricating contacts within the formed first and second patterns.

36. The device according to claim 31, wherein said two-dimensional electron gases grown on the undoped semi-insulating substrate form together an AlGaAs/GaAs heterostructure.

37. A method for inspecting a conductive sample for defects by determining a spatial distribution of a magnetic field vector within a vicinity of the conductive sample, wherein the magnetic field is produced by electric current passing through the conductive sample, the method comprising the steps of:

measuring a gradient of a magnetic field component along an axis substantially perpendicular to a surface of the conductive sample in at least two locations spaced-apart along an axis substantially parallel to the surface of the conductive sample, and generating measured data based on the measured gradient; and analyzing the measured data to determine a map of the magnetic field vector distribution indicative of distribution of the electric current inside the conductive sample, thereby detecting existence of the defect inside the sample and determining a location of the existing defect.

38. The method according to claim 37, wherein the step of analyzing the measured data includes comparing said map of the magnetic field distribution to a respective reference data representative of a similar non-defect sample.

39. The method according to claim 38, wherein said electric current is an eddy current induced by an external, alternating, magnetic field applied to said conductive sample.

40. The method according to claim 37, wherein the step of analyzing the measured data includes utilizing said map of the magnetic field distribution to calculate a profile of the electric current inside the conductive sample.

41. The method according to claim 40, wherein said electric current is a transport current generated by a power source directly coupled to said conductive sample.

* * * * *

UNITED STATES PATENT AND TRADEMARK OFFICE
CERTIFICATE OF CORRECTION

PATENT NO.   : 6,366,085 B1  
DATED        : April 2, 2002  
INVENTOR(S)  : Yosef Yeshurun et al.

It is certified that error appears in the above-identified patent and that said Letters Patent is hereby corrected as shown below:

<u>Column 10,</u>
Line 29, change "alone" to -- along --.

<u>Column 11,</u>
Lines 41, 47, 51, 56 and 59, change the claim dependency from "11" to -- 14 --.

<u>Column 12,</u>
Lines 4, 37 and 43, change the claim dependency from "11" to -- 14 --.

<u>Column 13,</u>
Line 14, change the claim dependency from "31" to -- 35 --.

Signed and Sealed this

Nineteenth Day of November, 2002

*Attest:*

*Attesting Officer*

JAMES E. ROGAN
*Director of the United States Patent and Trademark Office*